(12) United States Patent
Welle (10) Patent No.: US 11,567,054 B1
(45) Date of Patent: Jan. 31, 2023

(54) LENS FOR SHAPING AN EXPLOSIVELY GENERATED SHOCK

(71) Applicant: US Government by the Secretary of the Air Force, Wright Patterson AFB, OH (US)

(72) Inventor: Eric Welle, Niceville, FL (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 60 days.

(21) Appl. No.: 17/305,589

(22) Filed: Jul. 9, 2021

(51) Int. Cl.
  *G01N 33/22* (2006.01)
  *F42B 1/024* (2006.01)

(52) U.S. Cl.
  CPC ........... *G01N 33/227* (2013.01); *F42B 1/024* (2013.01)

(58) Field of Classification Search
  CPC ............................. G01N 33/227; F42B 1/024
  See application file for complete search history.

(56) References Cited

U.S. PATENT DOCUMENTS 5,565,644 A * 10/1996 Chawla .................. F42B 1/024
  102/307

FOREIGN PATENT DOCUMENTS

GB  2496250 A  *  5/2013  ............. G02B 17/00
RU  2244243 C1  *  1/2005

OTHER PUBLICATIONS

RU-2244243-C1—English (Year: 2005).*

* cited by examiner

*Primary Examiner* — Daniel S Larkin
*Assistant Examiner* — Fatemeh Esfandiari Nia
(74) *Attorney, Agent, or Firm* — AFMCLO/JAZ; Larry L. Huston (57) ABSTRACT

A shaped lens for minimizing differences in time of arrival at the output surface of an explosive assembly. The lens is plano-convex with the convex shape oriented towards the explosive charge. The lens becomes monotonically thicker as the center of the lens is radially approached from the edge, according to a formula accounting for the detonation velocity of the explosive and velocity of the shockwave through the lens. The lens is preferably incorporated into a test fixture using a liquid explosive, such as nitromethane. The test fixture may be assembled on site, at the test location.

20 Claims, 5 Drawing Sheets

LENS FOR SHAPING AN EXPLOSIVELY GENERATED SHOCK

STATEMENT OF GOVERNMENT INTEREST

The invention described and claimed herein may be manufactured and used by or for the Government of the United States of America for all government purposes without the payment of any royalty.

FIELD OF THE INVENTION

The present invention is directed to equalizing time arrival of a shockwave on a planar lens output surface of a test fixture and more particularly to equalizing the time arrival of a shockwave on an experimental planar lens output surface generated by a liquid explosive charge.

BACKGROUND OF THE INVENTION

Performance testing of explosives has long been accomplished using a solid explosive charge for each test. Techniques to collect unreacted Hugoniot and Run-to-Detonation data include gun techniques and explosive wedge techniques. Gun based techniques are generally favored, but require specialized infrastructure that is not readily deployed. Separately, wedge experiments have been used to quantify the sustained pulse growth or Pop plot data for reactive materials and to also quantify unreacted Hugoniot for both inert and reactive materials.

But each of these experimental techniques requires using a solid charge comprising two explosives. Using a solid charge raises the concern that solid charges are dangerous to load. Furthermore, only very limited locations are authorized and capable of fabricating solid charges. Additionally solid charge explosive wedges are limited in diameter by the available compressive pressure. Gun based experiments are limited to a fixed diameter based upon the bore of the gun under consideration. Once the solid charge, explosive wedge, is fabricated, it must be transported from one of the authorized loading sites to the test site—encountering even more risk. Transport and storage of such explosive charges are time consuming and costly hazardous operations.

In contrast, loading of an explosive test charge with a liquid explosive charge provides the benefit that loading can be locally accomplished at the test site. Locally loading a liquid charges reduces preparation time, allows more flexibility in last minute adjustments and reduces risk. And locally loading a liquid charge reduces risks associated with storage and shipment.

Experimental testing using a liquid explosive may be accomplished using an inert lens. The inert lens under consideration has a convex surface facing towards the charge and an opposed planar output surface. A performance metric of such an explosive lens is the simultaneity of the time of arrival (ToA) across the output surface of the lens.

But none of these attempts have proven satisfactory in reducing ToA disparities to desired tolerances particularly as the perimeter of the lens is approached. The present invention seeks to overcome this disparity in ToA.

SUMMARY OF THE INVENTION

In one embodiment the invention comprises an experimental plano-convex lens for reducing time variation in transmitting a shock wave from a first surface facing an explosive charge to an opposed second surface. The first surface and second surface define a radially varying thickness therebetween, with the first surface being axisymmetrically convex and the second surface being macroscopically planar. The first surface of the lens satisfies difference in time of arrival equations, to minimize differences in time of arrival at predetermined radial positions on the second surface. In another embodiment the invention comprises a test fixture having such a lens.

BRIEF DESCRIPTION OF THE DRAWINGS

All figures are drawn to scale unless specifically called out as schematic.

DETAILED DESCRIPTION OF THE INVENTION

Figure 1:
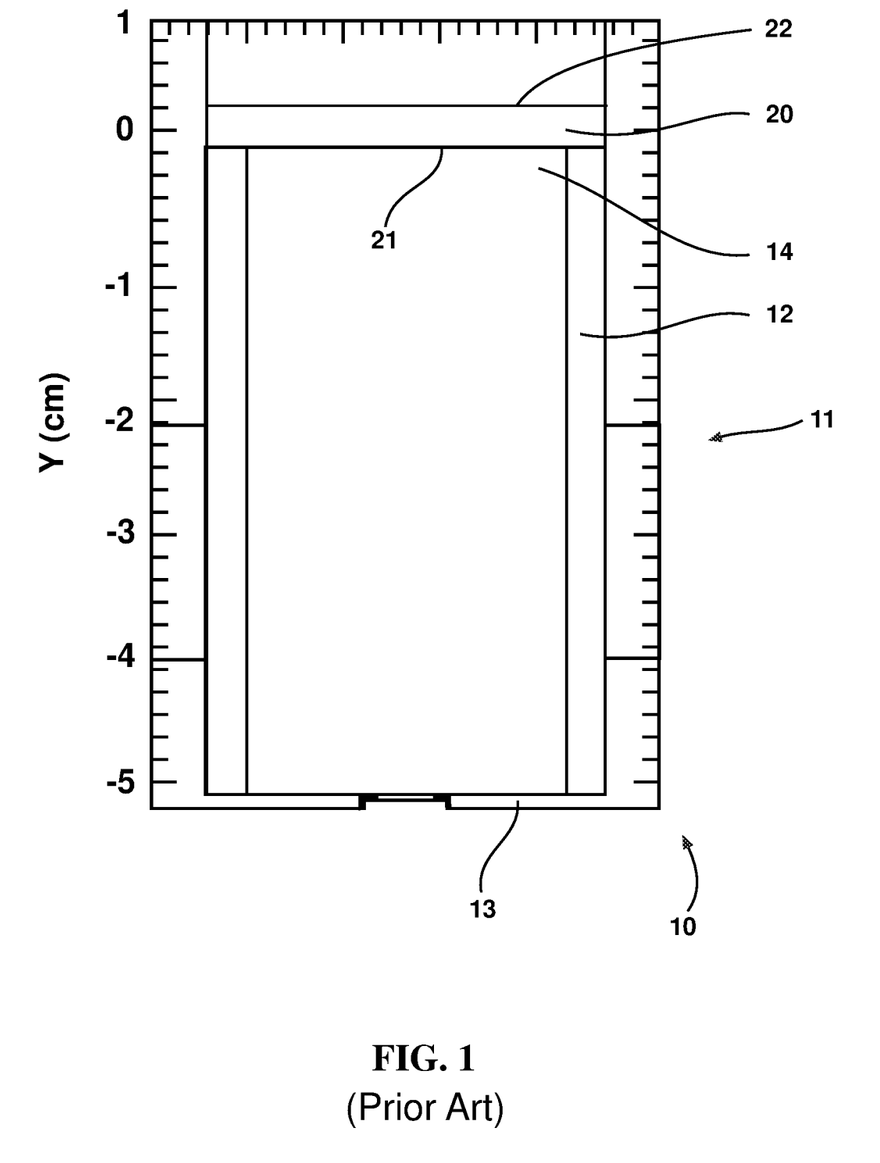
FIG. 1 is a frontal sectional view of a test fixture according to the prior art.
Figure 1A:
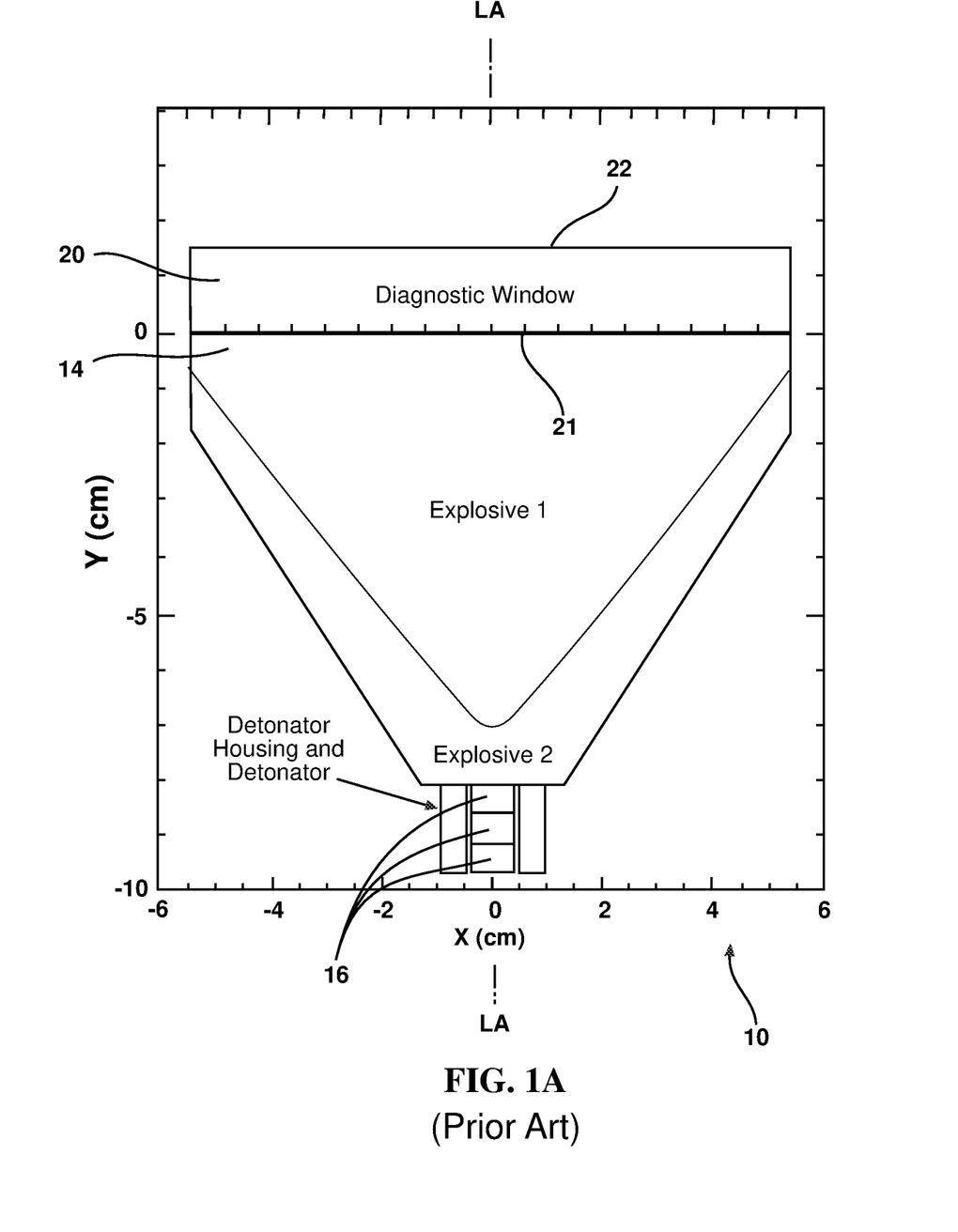
FIG. 1A is a schematic frontal sectional view of a lens according to the prior art.

Referring to FIGS. 1 and 1A, an experimental test fixture 10 may have a central longitudinal axis LA and may be axisymmetric. While a cylindrically shaped test fixture 10 having a constant cross section is shown, the invention is not so limited except as specifically claimed herein. For example the cross section of the test fixture 10 may be rectangular, square, equilaterally triangular or elliptical so long as it does not compromise simultaneity performance. The test fixture 10 may comprise a housing 11 having a closed end bottom 13 with upstanding sidewalls 12 and an opening 14 axially opposed to the bottom 13.

The closed end bottom 13 and upstanding sidewalls 12 may be integral or assembled from two or more component parts. If component parts are used, the closed end bottom 13 may be joined to and cup the sidewall 12 cylinder as shown. The closed end bottom 13 and separate sidewall 12 may be securely joined together with a shrinkfit, adhesive, welding, etc. This arrangement provides the benefit that different combinations of cups and sidewalls 12 may be used in a single test fixture 10. If an integral closed bottom 13 and sidewall 12 construction is used, this arrangement provides the benefit that a mismatched fit or insecure attachment is obviated.

The closed end bottom 13 and upstanding sidewalls 12 define and subtend a hollow chamber therein. For any cross section, the sidewalls 12 of the test fixture 10 have an inner sidewall 12 surface and an outer sidewall 12 surface opposed thereto. The inner surface of the sidewall 12 and inner surface of the bottom 13 define the volume of the chamber. The axial length of the sidewall 12 may range from about 15 cm to about 70 cm, are only constrained by the requirements of the test item being shock loaded by the lens 20 assembly and are preferably about 4 to about 7 cm.

The diameter of the chamber should be large enough to provide semi-ideal behavior for the particular charge 16 under consideration. If the diameter is too small, detonation will not occur or multi-dimensional effects will adversely affect the experiment. For a round cross section, the inner diameter of the sidewall 12 may range from about 10 to about 35 cm, with a diameter of 25 cm+/−5 cm having been found suitable. The length to diameter ratio may range from about 1.5 to about 2.5, with a length to diameter ratio of about 2 having been found suitable. This arrangement provides an experimental test volume ranging from about 2 mL to about 85 liters, with a volume of about 4 to about 6 liters, particularly 5 liters having been found suitable.

The closed end bottom 13 may further comprise a bung hole. The bung hole may have a diameter of about 3 to about 13 mm. The bung hole allows filling of the test fixture 10 with a liquid explosive, as discussed below. After filling the bung hole may be sealed.

A lens 20 may cover the opening 14 throughout the outer diameter of the sidewall 12 and throughout the outer circumference thereof. The lens 20 is preferably concentric the longitudinal axis LA and has a first surface 21 facing towards the closed end bottom 13 and a second surface 22 facing outwardly and opposed thereto.

A second volume is subtended by the region from the second surface 22 of the lens 20 to the free end of the sidewall 12. The second volume has an open end axially opposed to the second surface 22 of the lens 20. The second volume may contain an acceptor or even be filled with an acceptor.

A lens 20 may designate T=0 as corresponding to the instantaneous arrival of the shock wave against the center of the first surface 21 of the lens 20. For the prior art at radial distances 10 to 12 mm outward from the center, the shockwave may arrive at least 13 to 23 microseconds later than at the center of the lens. This difference in ToA is unsatisfactory for precision experimentation.

Figure 2:
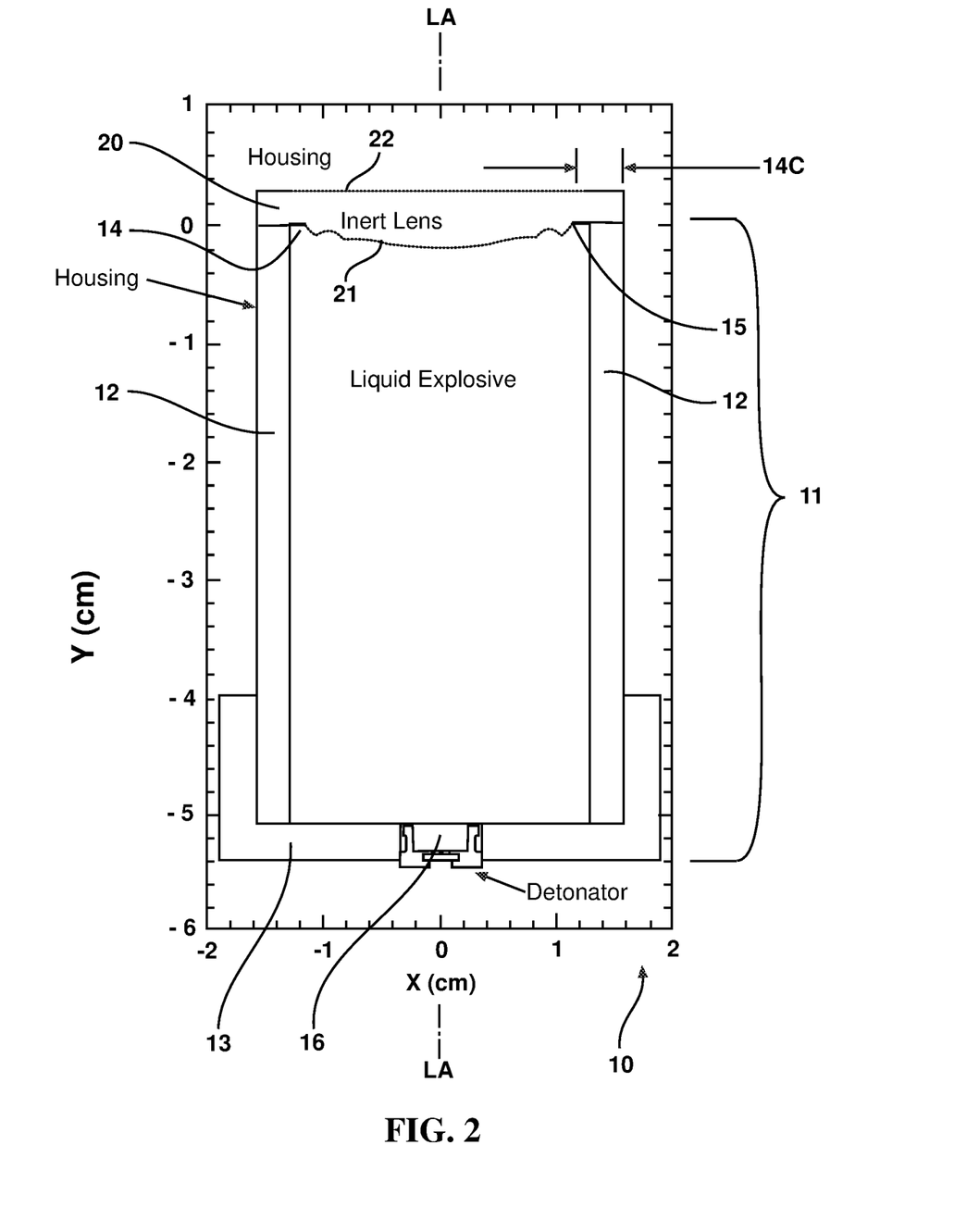
FIG. 2 is a frontal sectional view of a test fixture according to the present invention.

Referring to FIG. 2, the test fixture 10 according to the present invention has a lens 20 as described and claimed below. The lens 20 is plano-convex with a first surface 21 and a second surface 22 opposed thereto. Particularly the lens 20 has a second surface 22 which is macroscopically planar, meaning the surface is flat within ordinary manufacturing tolerances. The first surface 21 of the lens 20 is axisymmetric and preferably concentric with the sidewalls 12 and bottom 13 of the test fixture as well as the longitudinal axis LA. Likewise, the second surface 22 of the lens 20 is preferably axisymmetric, concentric and perpendicular to the longitudinal axis LA. The lens 20 has a border 15, defining a perimeter having a diameter of about 2 cm to about 12 cm and preferably about 3 cm to about 6 cm.

An optional collar 14 is preferably provided circumjacent the border 15 of the lens 20. The collar 14 may have a radial dimension of about 10 mm to about 15 mm and preferably about 12 mm to about 13 mm for a radial dimension of about 1 mm. As shown, the inner diameter of the collar 14 coincides with the outer diameter of the border 15 of the lens 20. The collar 14 may have a constant axial thickness of about 5 to about 20 mm and preferably about 6 to about 12 mm.

The inner diameter and outer diameter of the collar 14 are preferably coincident the inner diameter and outer diameter of the sidewall, respectively. Accordingly, the annular collar 14 serves the purpose of providing an attachment surface to mate with the annular end of the sidewall.

Figure 3:
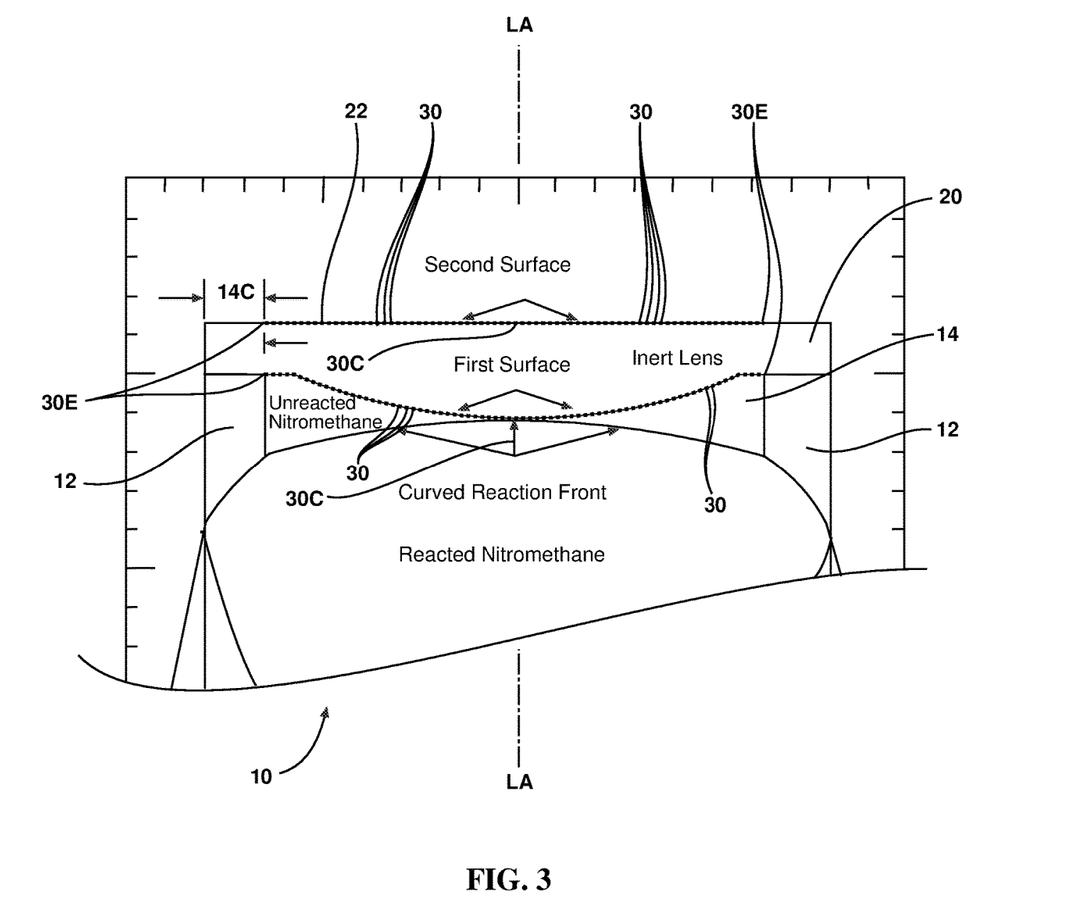
FIG. 3 is an enlarged fragmentary view of the lens, explosive charge and housing wall of the test fixture of FIG. 2.

Referring to FIG. 3, the first surface 21 of the lens 20 has a particularly preferred shape to minimize differences in ToA between the center and perimeter of the lens 20. The shape of the lens 20, particularly the axial thickness at any radius, is preferably determined in concert with the lens 20 material and the speed of the shockwave velocity through that particular lens 20 material. It is to be understood that for the degenerate case of a round lens 20, any circumference will have a constant thickness throughout.

Referring back to FIG. 4, to determine the shape of the shape of the lens 20, particularly, the convex face 22 thereof, a plurality of radially spaced pairs of nodes 30 are defined. For each pair, two nodes 30 lie on a common line parallel to the axial direction, one node 30 of the pair being disposed on the first surface 21 of the lens 20 and one node 30 of the pair being disposed on the second surface 22 of the lens 20.

Figure 4:
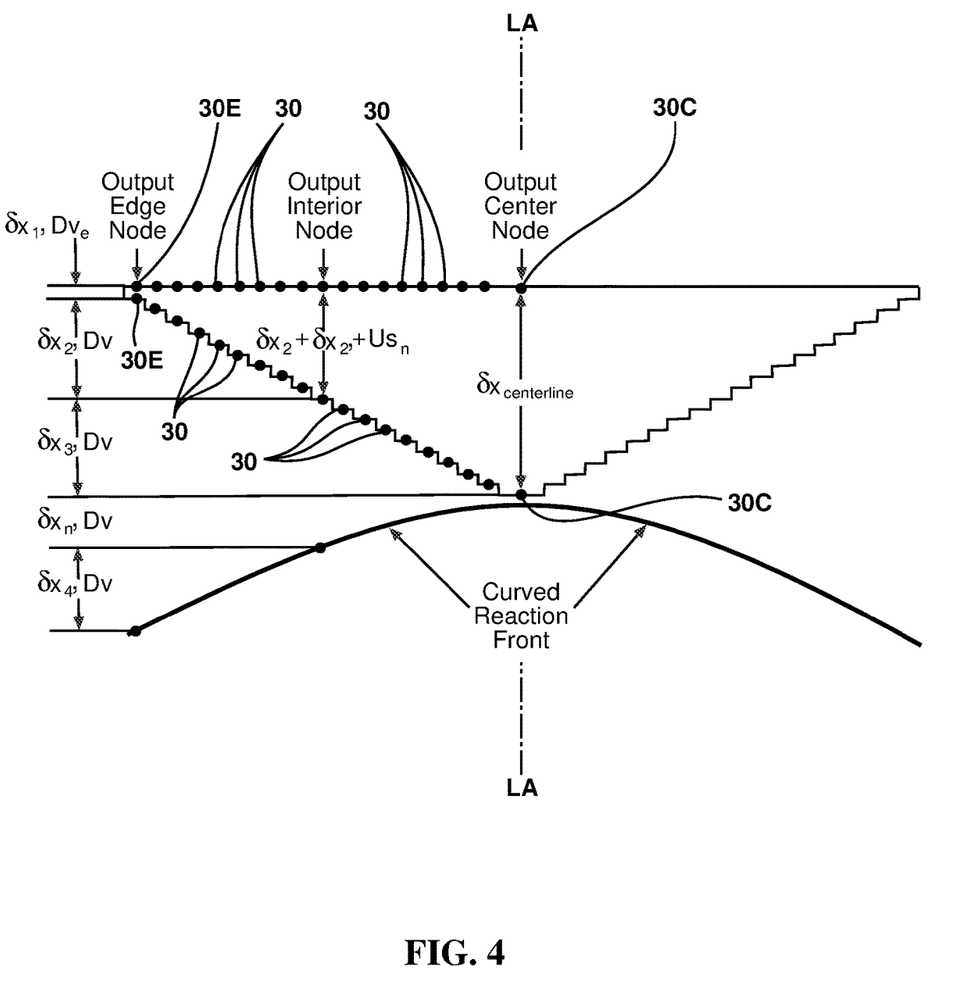
FIG. 4 is a stepped nodal representation of the geometry of the lens shown in FIG. 3.

The edge nodes 30E comprise the outermost pair of nodes 30 and lie on an axial line tangent the radius which transitions to increasing thickness as the center of the lens 20 is approached. The center nodes 30C comprise the inner most pair of nodes 30 and lie on the axis LA through the center of the lens 20. Intermediate the center nodes 30C and edge nodes 30E are a plurality of intermediate nodes 30I. The intermediate nodes 30I lie on a common radius between the center nodes 30C and edge nodes 30E.

The number of intermediate node pairs 30I is at least the minimum number of nodes 30 on the first surface 21 which have a difference in ToA between adjacent nodes 30, or preferably between the center node 30C and edge node 30E, on the same radius of less than about 10 nanoseconds. The 10 nanosecond maximum difference in ToA is generally accepted as providing adequate resolution for experimental purposes. More node pairs 30 may be used to provide increased resolution along the radius under consideration. Generally a difference in ToA less than about 10 nanoseconds will be adequate for many experimental purpose with a difference in ToA less than about 8 nanoseconds being preferred and less than about 6 nanoseconds being preferred and less than 5 nanoseconds being particularly preferred. Particularly, the maximum ToA difference cited above may occur at radial dimensions great than about 4 mm, about 5 mm, about 6 mm, about 8 mm, about 10 mm, about 12 mm, to about 13 mm from the center of the second surface 22.

Ordinary machining capabilities have a resolution of about 0.025 millimeters, which corresponds to a difference in ToA of about 4 nanoseconds. Thus one typically does not try to improve a difference in ToA less than about 4 nanoseconds to about 5 nanoseconds unless extraordinary machining is used. The time difference along any radius, from the center node 30I to the edge node 30E, may be calculated by subtracting the ToA of the shock at the second surface 22 from the ToA at the node of interest or may be empirically determined.

The ToA may be measured using a streak camera, velocity interferometer or similar instrumentation, having a window of approximately 1 microsecond and a temporal resolution no more than 100 picoseconds. A Hamamatsu C7700 streak camera and a Miteq photoreceiver having a bandwidth of at least 18 GHz powered by a NKT Photonoics laser system have been found suitable.

Referring to FIG. 4, the distance in the axial direction, or thickness, between the first surface 21 and second surface 22 taken at the pair of edge nodes 30E is designated $\delta x_1$. The distance in the axial direction, i.e. the thickness, taken at the pair of intermediate nodes 30I is designated $\delta x_1 + \delta x_2$. The distance in the axial direction, or thickness, taken at the pair of center nodes 30C is designated $\delta x_1 + \delta x_2 + \delta x_3$. At time T=0, the leading vertex of the shock wave is coincident the center of the lens 20, and the balance shock wave parabolically trails the center vertex as a function of increasing radius.

For maximum efficacy, the shock wave will simultaneously arrive at all points throughout the second surface 22. As the difference in ToA between the center node 30C and edge node 30E approaches zero on the second surface 22, efficacy approaches a maximum value for the particular test fixture 10 under consideration. To maximize efficacy and drive the difference in ToA to zero throughout all radial positions, one must satisfy the following equations:

$$\Delta t_{edge} = \delta t_{1e} + \delta t_{2e} + \delta t_{3e} + \delta t_{4e} = \delta t_{1n} + \delta t_{2n} + \delta t_{3n} + \delta t_n = \Delta t_n \quad 1)$$

$$\Delta t_{edge} = \frac{\delta x_1}{Us_e} + \frac{\delta x_2}{Dv} + \frac{\delta x_3}{Dv} + \frac{\delta x_4}{Dv} = \frac{\delta x_1}{Us_n} + \frac{\delta x_2}{Us_n} + \frac{\delta x_3}{Dv} + \frac{\delta x_n}{Dv} = \Delta t_n \quad 2)$$

wherein $\delta x_1$, $\delta x_2$ and $\delta x_3$ are geometrically defined in FIG. 2 above and functionally;

$\delta x_1$ is the thickness of the lens 20 at the edge;

$\delta x_2$ is the additional thickness to force simultaneity at the intermediate node pairs 30l;

$\delta x_3$ is the path length associated with the reactive shock that is common to both the edge node pair 30E and intermediate node pair 30l;

$\delta x_4$ is the path length of the shock wave to the axial position coincident the center of the first surface 21, as taken at the edge node 30E of the first surface 21;

$\delta x_n$ is the path length of the shock wave to the axial position coincident the center of the first surface 21, as taken at the intermediate node 30E of the first surface;

$Us_e$ is the average shock velocity through the lens 20 in the axial direction, taken at the edge node 30E pair;

$Us_n$ is the average shock velocity through the lens 20 in the axial direction, taken at the intermediate node pair 30l under consideration;

Dv is the detonation velocity of the explosive;

$\Delta t_{edge}$ is the time necessary for the shock to travel from its location along an axial path coincident with an edge node pair 30E and emerge on the second surface 22 of the lens 20 once the reactive shock reaches the T=0 condition, i.e. when the shock intercepts the the center of the first surface 21 at the center node 30C and may be thought of as the time for the shock wave at the edge node 30E to travel longitudinally through the respective δy path length wherein y corresponds to the counter 1, 2, 3 . . . ; and At, is the time necessary for the shock to travel from its location along an axial path coincident with an intermediate node pair 30C and emerge on the second surface 22 of the lens 20 once the reactive shock reaches the T=) condition, i.e. when the shock intercepts the the center of the first surface 21 at the center node 30C and may be thought of as the time for the shock wave at the intermediate node 30l to travel longitudinally through the respective δy path length wherein y corresponds to the counter 1, 2, 3 . . . ;.

The calculations parameterizing the Arrhenius model capture $\delta x_4$ and $\delta x_n$ so that these parameters are the path lengths associated with the shock wave of the edge node 30E and intermediate node 30l, respectively.

If these equations are solved for $\delta x_2$ to specify the shock path length at the intermediate node 30l to force simultaneity with the edge node, the lens 20 thickness may be designed according to $$\delta x_2 = \frac{Dv \cdot Us_n}{Dv - Us_n} \cdot \left[ \frac{\delta x_4 - \delta x_n}{Dv} + \frac{\delta x_1 \cdot (Us_n - Us_e)}{Us_e \cdot Us_n} \right]. \quad 3)$$

Using Equation 3, ToA differences at the second surface 22 are minimized and the desired shock effect is maximized.

For the degenerate case where $Us_e = Us_n$ Equation 3 can be simplified to:

$$\delta x_2 = \frac{Us_n}{Dv - Us_n} \cdot (\delta x_4 - \delta x_n). \quad 4)$$

For the geometries described and claimed herein, Equations 3 and 4 may be solvable using 10 to 300 intermediate nodes 30l, 20 to 200 intermediate nodes 30l, 25 to 100 intermediate nodes 30l and more particularly 50 to 75 intermediate nodes 30l. One will recognize the number of nodes 30 on any radius on the first surface 21 of the lens 20 is inversely proportional to increasing the accepted ToA differences on the radius of the first surface 21 of the lens 20.

Additional lens 20 thickness at the intermediate node 30l and center node 30C is directly proportional to $\delta x_4 - \delta x_n$, representing the curvature of the shock wave. As the donor explosive becomes more ideal and the radius of curvature approaches infinity the added thickness to the lens 20, $\delta x_2$, trends towards zero. Furthermore, as the difference between the unreacted shock velocity of the lens 20 and the detonation velocity of the donor explosive increases, $\delta x_2$ inversely proportionately decreases. Consequently, the present invention provides unexpected flexibility in designing the shape of the lens 20 to accommodate a particular combination of lens 20 material and donor explosive, so that the explosive more completely fills the lens 20 surface 22.

Table 1 below shows the ratio of thickness of the center node pair 30C to edge node pair 30E for various material using a sensitized nitromethane explosive.

TABLE 1

| Material | Thickness mm | Pressure GPa | $Us_n$ km/sec | $Us_n/(Dv-Us_n)$ dimensionless |
|---|---|---|---|---|
| PTFE | 2.54 | 6.7 | 4.1 | 1.9 |
| PMMA | 2.54 | 7.9 | 5.0 | 4.1 |
| AL6061 | 2.54 | 5.7 | 6.6 | −22.4 |
| SS304L | 2.54 | 2.9 | 5.4 | 5.9 |

An inert lens 20 of PTFE may act as the first buffer plate to control shock pressure in the acceptor. It will be understood that as $Us_n/(Dv-Us_n)$ approaches unity, a thicker lens 20 is required. Because the resultant shock velocity in AL6061 is slightly greater than that of sensitized liquid nitromethane (NM) a lens 20 having a concave first surface would be required for this combination.

A suitable explosive charge 16 to be used with the present invention is liquid nitromethane, (NM), alone or in combination with diethylenediamine (DETA) and/or other sensitizing agents. Using a liquid explosive according to the present invention avoids costs associated with shipment and storage of solid explosive materials and enables onsite construction of the explosive assembly. Additionally, the low viscosity NM easily conforms to the lens 20 surface, particularly when using a Newtonian fluid such as NM. In contrast, cast cure systems according to the prior art may be more prone to casting irregularities around contoured surfaces, such as the first surface 21 of the lens 20. Finally, the NM system does not require a curing process where differences in coefficient of thermal expansion and thermal diffusivity may affect the critical donor/inert lens 20 interface, as occurs in the prior art. If DETA is used in addition to the NM, the DETA may comprise from about 4 weight percent to about 7 weight percent of the liquid explosive.

One will recognize the test fixture 10 made according to the present invention is scalable and usable with various sizes of test fixtures 10 and charges 16. For example, one may wish to use a larger diameter cross section, and thus larger chamber volume, for insensitive explosives.

The inside of the chamber may have a generally elliptical cross section, it being understood that the experiment will be limited by the minor diameter of the ellipse. This arrangement has the benefit that the charge 16 may be increased compared to a circular cross section, having the same diameter as the minor diameter of the ellipse. The cross section of the test fixture 10 may be constant as shown or may be varied to decrease as the lens 20 is approached, for example to be frustoconically shaped.

Independent of the interior cross section of the chamber, the outside of the experimental test fixture 10 may be concentric with and congruent with the internal cross section of the chamber. Alternatively, the outside of the test fixture 10 may have one or more flat sides. This arrangement provides the benefit that sensitive instrumentation may be more easily attached to the outside of the test fixture 10 for probing the second surface 22 or to accommodate other experimental needs.

The invention is not limited by the foregoing description, and may include all combinations and permutations of the foregoing variants. Where feasible, singular and plural elements may be used interchangeably and all ranges are approximate, whether or not individually stated. Furthermore the lower bound of any range may be paired with and is matchable with the upper bound of any other range. And the upper bound of any range may be paired with and is matchable with the lower bound of any other range.

What is claimed is:

1. An experimental plano-convex lens for reducing time variation in transmitting a shock wave therethrough, said lens having a longitudinal axis defining a longitudinal direction and a center of the lens, the lens being circumscribed by a border and comprising:
   a first surface and a second surface opposed thereto and defining a thickness therebetween, said first surface being axisymmetrically convex, said second surface being macroscopically planar; said lens having a plurality of radially spaced apart pairs of nodes, one node of each pair disposed on said first surface and one node of each pair disposed on said second surface, the nodes of each pair being longitudinally aligned, the radially spaced apart nodes lying on a radius extending from a center pair of nodes to an edge pair of nodes, and a plurality of n intermediate radially spaced apart pairs of nodes therebetween, each of the nodes on the first surface satisfying the equation:

$$\delta x_2 = \frac{Dv \cdot Us_n}{Dv - Us_n} \cdot \left[ \frac{\delta x_4 - \delta x_n}{Dv} + \frac{\delta x_1 \cdot (Us_n - Us_e)}{Us_e \cdot Us_n} \right]$$

wherein $\delta x_1$ is the axial thickness of said lens taken at the border of said lens;

$\delta x_2$ is an incremental axial thickness greater than $\delta x_1$ and taken at a radial position;

$\delta x_4$ is an axial distance between the center of said second surface and the edge of an explosive reaction front at the border of said lens, taken when the center of an explosive reaction front is coincident said center of said lens;

$\delta x_n$ is an axial distance between said center of said second surface and the edge of an explosive reaction front at an nth intermediate node taken when the center of the explosive reaction front is coincident said center of said lens;

$Us_e$ is an average shock velocity through said lens, taken in the axial direction at said border of said lens;

$Us_n$ is an average shock velocity through said lens, taken in the axial direction at an nth intermediate node of said lens and Dv is the detonation velocity of a particular explosive under consideration, and the nodes on the first surface are radially spaced apart such that a time of arrival difference between adjacent nodes is less than 10 nanoseconds.

2. A lens according to claim 1 which is round.

3. A lens according to claim 2 having a diameter of 20 cm to 30 cm.

4. A lens according to claim 3 further comprising an annular collar circumjacent said border of said lens, said annular collar having a constant thickness in the axial direction.

5. A lens according to claim 4 which is inert, homogenious and comprises a material selected from the group consisting of PMMA and PTFE.

6. A lens according to claim 1 wherein said time of arrival difference between adjacent nodes is less than 6 nanoseconds.

7. An inert experimental plano-convex lens for reducing time variation in transmitting a shock wave therethrough, said lens having a longitudinal axis defining a longitudinal direction and a center of the lens, the lens being circumscribed by a border and comprising:
   a first surface and a second surface opposed thereto and defining a thickness therebetween, said first surface being axisymmetrically convex, said second surface being macroscopically planar; said lens having a plurality of radially spaced apart pairs of nodes, one node of each pair disposed on said first surface and one node of each pair disposed on said second surface, the nodes of each pair being longitudinally aligned, the radially spaced apart nodes lying on a radius extending from a center pair of nodes to an edge pair of nodes, and a plurality of n radially spaced apart intermediate pairs of nodes therebetween, each of the nodes on the first surface satisfying the lens thickness equation:

$$\delta x_2 = \frac{Dv \cdot Us_n}{Dv - Us_n} \cdot \left[ \frac{\delta x_4 - \delta x_n}{Dv} + \frac{\delta x_1 \cdot (Us_n - Us_e)}{Us_e \cdot Us_n} \right]$$

wherein $\delta x_1$ is the axial thickness of said lens taken at the border of said lens;

$\delta x_2$ is an incremental axial thickness greater than $\delta x_1$;

$\delta x_4$ is an axial distance between the center of said second surface and the edge of an explosive reaction front at the border of said lens, taken when the center of an explosive reaction front is coincident said center of said lens;

$\delta x_n$ is an axial distance between said center of said second surface and the edge of an explosive reaction front at an nth intermediate node taken when the center of the explosive reaction front is coincident said center of said lens;

$Us_e$ is an average shock velocity through said lens, taken in the axial direction at said border of said lens;

$Us_n$ is an average shock velocity through said lens, taken in the axial direction at an nth intermediate node of said lens and $Dv$ is the detonation velocity of a particular explosive under consideration, and the nodes on the first surface are radially spaced apart such that a time of arrival difference between adjacent nodes is less than 10 nanoseconds.

8. A lens according to claim 7 wherein said difference in said time of arrival is less than 6 nanoseconds.

9. A lens according to claim 8 wherein said difference in said time of arrival is less than 5 nanoseconds at a radius of 7 mm to 14 mm.

10. A lens according to claim 7 satisfying said equation with 20 to 200 intermediate nodes.

11. A lens according to claim 10 satisfying said equation with 50 to 75 intermediate nodes.

12. A lens according to claim 10 further having an edge thickness satisfying an edge thickness equation;

$$\delta x_2 = \frac{Dv \cdot Us_n}{Dv - Us_n} \cdot \left[ \frac{\delta x_4 - \delta x_n}{Dv} + \frac{\delta x_1 \cdot (Us_n - Us_e)}{Us_e \cdot Us_n} \right].$$

13. A lens according to claim 12 satisfying said lens thickness equation, said edge thickness equation having 25 intermediate nodes to 100 intermediate nodes.

14. A lens according to claim 12 wherein $Us_e = Us_n$.

15. An experimental test fixture for holding and experimenting with a liquid explosive charge, said test fixture having a longitudinal axis defining a longitudinal direction and comprising:

a housing having a closed end bottom, an opening axially opposed thereto and sidewalls extending from said bottom to and circumscribing said opening to define a chamber therein; and a plano-convex lens for reducing time variation in transmitting a shock wave therethrough, covering said opening, said lens having a longitudinal axis defining a longitudinal direction and a center of the lens, the lens being circumscribed by a border and comprising:

a first surface and a second surface opposed thereto and defining a thickness therebetween, said first surface being axisymmetrically convex, said second surface being macroscopically planar;

said lens having a plurality of radially spaced apart pairs of nodes, one node of each pair disposed on said first surface and one node of each pair disposed on said second surface, the nodes of each pair being longitudinally aligned, the radially spaced apart nodes lying on a radius extending from a center pair of nodes to an edge pair of nodes, and a plurality of n intermediate radially spaced apart pairs of nodes therebetween, said nodes on the first surface satisfying the lens thickness equation:

$$\delta x_2 = \frac{Dv \cdot Us_n}{Dv - Us_n} \cdot \left[ \frac{\delta x_4 - \delta x_n}{Dv} + \frac{\delta x_1 \cdot (Us_n - Us_e)}{Us_e \cdot Us_n} \right]$$

wherein $\delta x_1$ is the axial thickness of said lens taken at the border of said lens;

$\delta x_2$ is an incremental axial thickness greater than $\delta x_1$;

$\delta x_4$ is an axial distance between the center of said second surface and the edge of an explosive reaction front at the border of said lens, taken when the center of an explosive reaction front is coincident said center of said lens;

$\delta x_n$ is an axial distance between said center of said second surface and the edge of an explosive reaction front at an nth intermediate node taken when the center of the explosive reaction front is coincident said center of said lens;

$Us_n$ is an average shock velocity through said lens, taken in the axial direction at an nth intermediate node of said lens and $Dv$ is the detonation velocity of a particular explosive under consideration, and the nodes on the first surface are radially spaced apart such that a time of arrival difference between adjacent nodes is less than 10 nanoseconds.

16. A test fixture according to claim 15 wherein said lens is concentric with said longitudinal axis.

17. A test fixture according to claim 16 having a volume of 4 L to 6 L.

18. A test fixture according to claim 15 wherein time of arrival difference between adjacent nodes is less than 6 nanoseconds.

19. A test fixture according to claim 18 further comprising a liquid explosive charge therein, wherein said liquid explosive charge comprises NM.

20. A test fixture according to claim 19 wherein said liquid explosive charge further comprises 4 weight percent to 7 weight percent DETA.

\* \* \* \* \*